United States Patent
Zieris

(10) Patent No.: US 9,861,365 B2
(45) Date of Patent: Jan. 9, 2018

(54) ONE-PIECE SURGICAL CLIP

(71) Applicant: Aesculap AG, Tuttlingen (DE)

(72) Inventor: Gerold Zieris, Mühlheim (DE)

(73) Assignee: AESCULAP AG, Tuttlingen (DE)

(*) Notice: Subject to any disclaimer, the term of this patent is extended or adjusted under 35 U.S.C. 154(b) by 272 days.

(21) Appl. No.: 14/388,460

(22) PCT Filed: Apr. 26, 2013

(86) PCT No.: PCT/EP2013/058738
§ 371 (c)(1),
(2) Date: Sep. 26, 2014

(87) PCT Pub. No.: WO2013/160452
PCT Pub. Date: Oct. 31, 2013

(65) Prior Publication Data
US 2015/0057684 A1 Feb. 26, 2015

(30) Foreign Application Priority Data
Apr. 27, 2012 (DE) .................. 10 2012 103 727

(51) Int. Cl.
*A61B 17/08* (2006.01)
*A61B 17/122* (2006.01)

(52) U.S. Cl.
CPC ........ *A61B 17/083* (2013.01); *A61B 17/1227* (2013.01)

(58) Field of Classification Search
CPC ... A61B 17/083; A61B 17/10; A61B 17/1285; A61B 17/122; A61B 17/1227; A61B 17/00234; A61B 17/0644
See application file for complete search history.

(56) References Cited

U.S. PATENT DOCUMENTS

| 3,604,071 A | 9/1971 | Reimels |
| 4,337,774 A * | 7/1982 | Perlin .................. A61B 17/122 24/536 |
| 4,835,824 A | 6/1989 | Durham et al. |
| 5,236,440 A * | 8/1993 | Hlavacek ........... A61B 17/0644 227/902 |

(Continued)

FOREIGN PATENT DOCUMENTS

| DE | 2036725 A1 | 2/1971 |
| DE | 19858580 C1 | 9/2000 |

(Continued)

OTHER PUBLICATIONS

Chinese Office Action for Chinese Application No. 201380020126.9, dated May 5, 2016, 14 pages.

(Continued)

*Primary Examiner* — Julie A Szpira
(74) *Attorney, Agent, or Firm* — RatnerPrestia

(57) ABSTRACT

A surgical clip includes two clip branches, each clip branch having a clamping portion, an actuating portion, and a flexural spring arrangement by which the two clip branches are coupled to each other preferably in one material piece. The flexural spring arrangement includes a coupling device by means of which selected portions of the flexural spring arrangement can be short-circuited for spring biasing and possibly for varying, preferably reducing, the active total spring length thereof.

16 Claims, 2 Drawing Sheets

(56) References Cited

U.S. PATENT DOCUMENTS

Figure 1:
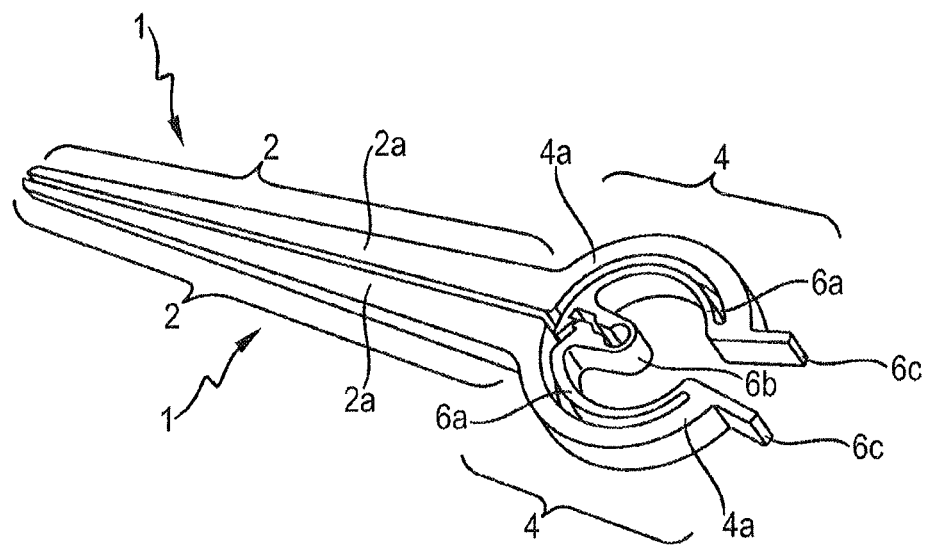

| | | | |
|---|---|---|---|
| 5,725,763 | A | 3/1998 | Bonhomme et al. |
| 6,179,850 | B1 | 1/2001 | Goradia |
| 6,210,419 | B1 | 4/2001 | Mayenberger et al. |
| 7,713,284 | B2 | 5/2010 | Crofford |
| 9,572,579 | B2 | 2/2017 | Weisshaupt |
| 2008/0077144 | A1* | 3/2008 | Crofford .............. A61B 17/064 606/75 |
| 2011/0152887 | A1 | 6/2011 | Surti |
| 2012/0184976 | A1 | 7/2012 | Nakamura |
| 2013/0172914 | A1 | 7/2013 | Weisshaupt |

FOREIGN PATENT DOCUMENTS

| | | |
|---|---|---|
| DE | 202010008512 U1 | 12/2010 |
| DE | 2010008714 U1 | 1/2011 |
| EP | 0122046 | 10/1984 |
| JP | 1984168848 | 9/1984 |
| JP | H01310654 | 12/1989 |
| JP | H06007360 | 1/1994 |
| JP | 3157486 U | 2/2010 |
| WO | 2011068073 A1 | 6/2011 |
| WO | 2012031949 | 3/2012 |
| WO | 2012045500 A1 | 4/2012 |

OTHER PUBLICATIONS

German Search Report with partial translation issued in related German Application No. 10 2012 103 727.2, dated Feb. 7, 2013.
International Search Report and Written Opinion with partial translation in related International Application No. PCT/EP2013/058738, dated Aug. 29, 2013.
Notice of Reasons for Rejection for Japanese Application No. 2015-507554, dated Mar. 10, 2017, 3 pages.
European Office Action with English language translation for Application No. 13 719 531.9, dated Aug. 30, 2017, 9 pages.

* cited by examiner

ONE-PIECE SURGICAL CLIP

RELATED APPLICATIONS

This is the U.S. National Phase of International Application No. PCT/EP2013/058738, filed Apr. 26, 2013, which claims the benefit of German Application No. DE 10 2012 103 727.2, filed Apr. 27, 2012, the contents of both applications being incorporated by reference herein in their entireties.

FIELD

The invention relates generally to a surgical clip, and more specifically to a one-piece aneurysm clip.

BACKGROUND

Surgical clips (also referred to as tissue clip) are medical implants that are used in most cases temporarily for closing tissue perforations, for example, or for the treatment of aneurysms as vessel clips. For this purpose a plurality of clip shapes are suited starting with jaw-like clips in which the clamping or clip branches are in the form of two opposed longitudinally curved rows of teeth similarly to the upper and lower jaws, which are coupled to each other via hinges at their respective two longitudinal ends, up to row-shaped (straight) clips that include two opposed substantially straight clamping rails comparable to conventional forceps, the clamping attachments being provided with teeth or a corrugation, where appropriate, and being coupled to each other hinge-like at one respective longitudinal end only.

All known clip shapes have in common, however, at least one spring arrangement applying a clamping force to the clip branches. This at least one spring arrangement can be a separate component inserted in the clip so as to pre-stress the clip branches against each other or it is integrated (in one piece) in the clip. In the latter case the spring arrangement substantially forms the hinge or hinges to which the two clip branches are pivoted.

From the state of the art a surgical clip of the species having straight clip branches and a one-sided spring arrangement is known, as it is published in DE 20 2010 008 512 U1, for example.

The clamping or closing force is generated in this case by a leg spring in the form of either a round or a rectangular spring. Concretely speaking, such clip consists of two clip branches that are loosely intersecting (i.e. without any mechanical connection such as a hinge pin) in their respective central portions so as to form two clamping portions adjacent in parallel in the closing position and two actuating legs or actuating portions spaced apart from each other in this position. The free ends of the actuating portions are interconnected by the afore-mentioned leg spring which is formed either integrally (of one single part) with the clip branches or as separate component and then is connected (soldered, welded, put together etc.) to the clip branches so as to form one member. The leg spring may have either half a winding, a 1.5 fold or even 2.5 fold winding.

For operation the surgical clip is compressed at its actuating portions, thereby the clamping portions being spaced apart from each other due to the intersecting orientation of the clip branches. At the same time the leg spring is biased more strongly. When the actuating portions are released, the leg spring causes the actuating portions to be urged apart until the clamping portions are pressed against each other.

Although the afore-mentioned design ensures sufficiently high pressing force between the two clamping portions and the leg spring is little loaded due to an only small elastic degree of deformation and therefore is very long-living, there are still resulting several drawbacks.

The use of the leg spring requires a comparatively expensive and difficult manufacturing process for winding the spring which has to be carried out without the spring material forming cracks. In this case, too, there is the possibility of rewinding the leg spring, thereby the pressing force between the clamping portions being reduced. In total, the manufacture of the leg spring therefore requires a high degree of precision so as to manufacture instruments the characteristics of which (pressing force, lifetime, reliability etc.) are within a narrow tolerance range. Therefore the scrap rate is correspondingly high. All afore-mentioned and further drawbacks of the known surgical clip finally result in a comparatively high price for the surgical clip.

Further surgical clips of this species are also known from U.S. Pat. No. 6,179,850 B1 or EP 0 122 046 A1, for example.

From a further state of the art document according to DE 20 2010 008 714 U1 a surgical clip is known comprising two clip branches extending in parallel to each other without intersecting and being interconnected in their respective central areas via a land-like flexural spring. Accordingly, the clip branches are extended beyond the flexural spring in the longitudinal direction thereof and thus form two clamping portions on the one side of the flexural spring and two actuating legs/portions on the other side of the flexural spring, for example according to the principle of a generally known peg. When the two actuating portions are thus pressed against each other on the one side of the land-like flexural spring, the two clamping portions are moving apart on the other side of the flexural spring and vice versa.

This surgical clip is manufactured of one single part according to an injection molding process and is thus relatively inexpensive as regards its manufacture. In contrast to the afore-described clip, the fabrication can be carried out substantially automatically and thus inexpensively by the injection molding process. The biasing of the flexural spring in the closed position of the clip is obtained by a locally differing material shrinkage upon hardening of the injection molded material in accordance with this disclosure. In this way, a comparatively high quality standard can be reached in a simple manner. However, this solution has drawbacks as well.

Although the flexural spring has an open annular shape bulging in the direction of the actuating portions, the deformation path/degree of the flexural spring in normal use is comparatively large so that the spring can rapidly fatigue. Moreover, the flexural stress is by far higher vis-à-vis the leg spring, which also results in more frequent spring fractures. Finally this is resulting in lower reliability and service life compared to the leg spring. In particular, it has also turned out to be difficult to attain sufficient reproducible clamping forces by the afore-described non-symmetric material shrinkage.

Furthermore, in the state of the art efforts have been made to arrange the annular or U-shaped flexural spring at the respective outer ends of the clip branches so that clamping and actuating portions of each clip branch are located on the same side of the spring and thus have the same direction of movement when the clip is actuated (and not opposed directions as in the aforementioned state of the art). In this case the clip is spread by pulling the actuating portions apart and not by compressing them as in the state of the art cited in the beginning. This entails the fact that the clip becomes unhandy and non-ergonomic, thereby its field of use being definitely reduced. Alternatively there is basically the option to cross the branches so that compressing the actuating portions causes the clamping portions to open. However, also in this case at least the biasing force of the spring has turned out to be comparatively small so that the material strength of the spring had to be increased. Therefore the clip is in total dimensioned so large that it is suited for specific purposes only.

Another surgical clip is known from DE 198 58 580 C1. The clip described there is U-shaped and includes two clip branches extending in parallel without intersecting and being interconnected in their respective central areas via a land-shaped flexural spring. A detent means of the clip fixes the land upon compression of the clip branches so as to bring about comparatively high retaining forces. However, in this case too, it has turned out to be difficult to generate sufficiently reproducible clamping forces.

SUMMARY

In view of these problems, it is the object of the present invention to provide an inexpensive surgical clip having improved properties. It is an objective that the clip exhibits high reliability especially in retaining the function of the biasing spring and is most versatile. It is another objective that the clip offers maximum closing force and opening width with minimum design. Moreover, the clip should preferably have an (integrated) protecting mechanism to prevent mechanical overload, for example as a result of improper handling.

The object as well as the further objectives are achieved by a surgical clip, especially a one-piece and one-material aneurysm clip.

Basically it is a keynote of the invention to preferably use for a one-material surgical clip of the non-intersecting design a flexural spring or flexural spring (series) arrangement the total spring length of which is extended by a (preferably bellows-type) serial arrangement or sequence of individual springs (individual leaf springs) or spring arms for example by serial (one-material) joining/forming of a number of flexural springs (leaf springs), by plastic/permanent folding or bending (plastic deformation during the manufacturing process) of one single flexural spring to form a number of spring portions of singular action or similar front-face flexural spring combinations. On at least one (central) portion of the flexural spring (series) arrangement a coupling device is arranged or formed/integrally formed by means of which at least two individual (flexible) springs or spring portions (spring arms) can be directly connected/coupled, while at least one of these two individual (flexural) springs or spring portions (spring arms) is elastically biased and the active total spring length is possibly reduced.

In a one-material surgical clip there is basically the problem that the flexural spring (arrangement) initially is not biased in terms of manufacture during fabrication thereof (in the as-designed position) for instance according to the injection molding process. Therefore, most one-material surgical clips prefer the intersecting design for which the flexural spring (arrangement) has to be elastically deformed so that the initially parallel, not crossed clip branches can be intersected and now pressed against each other so-to-speak laterally inverted.

On the other hand, the present invention basically provides to bias the flexural spring (series) arrangement in itself after the one-material fabrication thereof with the branches in that the flexural spring arrangement is designed to be so-to-speak "open" in the manufacturing position (with one-material fabrication) and has to be subsequently tensioned for "closing", whereby sufficient spring bias can be obtained also with surgical clips of the non-intersecting design. That is, the coupling device of the flexural spring (series) arrangement serves for "short-circuiting" at least two flexural spring portions/arms while elastically deforming the same and thus for obtaining an (increased) spring bias in the closing direction of the clip.

In practical use substantially the at least two flexural spring portions/arms to be short-circuited are interconnected at their respective one ends during clip manufacture via a spacer (being part of the flexural spring (series) arrangement) which is deformed hinge-like (possibly also in a spring-elastic manner) when the two ends are short-circuited. By this technically constructional measure basically also the advantage can be achieved that the flexural spring (series) arrangement can exploit the entire (maximum) spring length (including the spacer), for instance when the clip branches coupled by this spring arrangement are moved apart, so that excessive bending of the spring arrangement is prevented and the spring force to be overcome is minimized. At the same time, the maximum spring force can be increased especially in the closing position of the clip branches in that the coupling device (for example upon reaching the closing position) is actuated and the flexural spring (series) arrangement is so-to-speak short-circuited thereby, i.e. part of the flexural spring (series) arrangement (i.e. the spacer) is removed from/switched out of the relevant flow of force. In this way theoretically different flexural spring (series) arrangement systems having different spring characteristics/rigidities relative to each other could be adjusted (or simulated) by the coupling device.

What is crucial, however, is the fact that the later biasing of the flexural spring arrangement not (only) has to be obtained by intersection of the clip branches, but is brought about by elastic joining of at least two flexural spring portions/arms via the coupling device according to the invention.

Preferably the coupling device is configured so that for the coupling closure (engaged state) thereof at least the one individual spring or the one spring portion has to be elastically deformed (preferably both spring portions/arms to be coupled), thereby the afore-mentioned biasing of the flexural spring (series) arrangement being achieved in the closing position of the clip branches the height of which depends on the dimensioning of the coupling device and/or the position thereof along the flexural spring (series) arrangement. In this way, the pre-tensioning force can be safely reached/increased in the closing position of the clip branches by engaging the coupling device in a predetermined manner.

Another or additional basic idea of the invention provides that the flexural spring or the flexural spring (series) arrangement extends inwardly, i.e. toward the clamping portions, at least in segments starting from the actuating portions of the clip branches.

In this manner the bending degree of the flexural spring/flexural spring (series) arrangement or of the individual springs can be reduced and thus the reliability can be increased. Also, due to the use of flexural springs a sufficiently strong biasing force can be achieved without the surgical clip having to be enlarged/extended.

The surgical clip in accordance with a special aspect of the invention consequently has two clip branches (not intersecting in the as-designed position), each comprising at least one clamping portion and one actuating portion, as well as the flexural spring (series) arrangement via which the two clip branches, especially the actuating portions thereof are coupled to each other (at the proximal ends thereof) in one material piece. The flexural spring (series) arrangement at least functionally and/or structurally constitutes at least two spring legs or arms which are serially interconnected (via the spacer). These at least two spring arms are further orientated/arranged on the clip so that they extend between the two opposed actuating portions in the direction of the clamping portions.

By this technical measure the maximum possible bending distance of the spring (i.e. the maximally active total spring arm length) is increased and thus the degree of deformation thereof and the degree of deformation of the individual spring arms (with opened/disengaged coupling device) is reduced. The total dimension of the clip is not or only insignificantly increased (extended), however, as the individual springs or spring portions/arms do not extend in the direction away (in the proximal direction) from the clamping portions, as this is the case in the state of the art, but in the opposite direction (in the distal direction). In this way a strong biasing force can be reached with little risk of breakage and compact design so that also the application of the clip is expanded due to this compact design. Since, moreover, the clip makes use of a flexural spring (substantially two-dimensional) and not of a spiral or leg spring having a complex (three-dimensional) geometry, it can be manufactured in a simple and thus inexpensive way.

It is of advantage when the functionally and/or structurally at least two serially arranged spring arms of the flexural spring or flexural spring arrangement (in their joint top view) form a C, U or V shaped layout, the bracket-shaped actuating portions being adapted to the top view shape of the spring arms. That is, the actuating portions extend integrally with the associated clamping portions from the respective root thereof in the proximal direction preferably C shaped or curved, wherein the respective one spring arm is integrally formed in one material piece at the proximal end of the corresponding actuating portion/bracket and extends in the opposite direction (in the distal direction) along the respective actuating portion (while a substantially uniform clearance is retained).

Such simple geometric basic form can be easily and precisely produced and thus further contributes to cost reduction. It is noted in this context that also other forms for the spring arms (and the actuating portions) such as a π or Ω shape are possible or the afore-mentioned basic forms can be superimposed by further sub-forms such as corrugated or zigzag spring arms, thereby the active spring length for each spring arm being adapted to be further increased. Moreover, by the design fact that the flexural spring/flexural spring arrangement of the surgical clip is integrally connected via its spring legs/arms to the axial free (proximal) ends of the actuating portions of the two branches, an especially favorable introduction of bending force to the flexural spring is achieved (without any additional lever action).

It is noted that the actuating portion of each clip branch can be rigid or spring-elastic at least over a partial distance (or completely) and thus can constitute part of the flexural spring arrangement. In other words, it is possible to functionally/structurally equip the flexural spring/flexural spring arrangement with two spring arms (as afore-described) so that the free ends of the spring arms extend in a direction away from the clamping portions of the clip branches. In this case the free ends of these two spring arms are connected to the rear end areas/ends of the actuating portions. When the actuating portions are manually compressed, an elastic flexural deformation is imparted to these two spring arms along their arm length, i.e. the turning is elastically spread. The degree of deformation of the flexural spring arrangement thus is exclusively resulting from the total length of these two spring arms in the case of comparatively rigid actuating portions.

However, it is also possible to design the actuating portions to be elastic at least over a partial length or completely, i.e. to deliberately associate them with an elastic deformation in the usual case of actuation. In this case a flexural spring or a flexural spring arrangement comprising the two afore-mentioned spring arms is resulting to the respective end side of which another flexural spring arm is serially connected so that in the layout a W-shaped flexural spring arrangement (including 4 individual springs) is formed. The orientation of the flexural spring arrangement remains unchanged. That is, the two outer spring arms now simultaneously constitute the actuating portions or at least a section thereof, the free (rear) ends thereof being serially coupled to the spring arms arranged between the actuating portions. In this way the degree of deformation of each individual spring arm can be further reduced.

Another possibly independent aspect of the invention relates to the special configuration of the coupling device.

Preferably the coupling device is arranged in the portion of the flexural spring (series) arrangement in which the at least two individual springs (spring portions) are serially interconnected, i.e. in a (central) portion located closest to the clamping branches. Concretely speaking, the at least two preferably C shaped individual springs or spring arms are further preferably serially interconnected (in one material piece) via an additional U or V shaped spring element as spacer which extends to the newly opposite direction (to the proximal direction), i.e. which opens toward the clamping branches (in the distal direction). In this way preferably two additional individual springs/spring arms are formed, thereby in the top view approximately the shape of a "ω" character being imparted to the flexural spring (series) arrangement. The coupling device now is arranged and/or configured so that this additional spring element can be short-circuited or bridged such that in the engaged state of the coupling device only the two outer (C shaped) individual springs are active and in the disengaged state the two inner individual springs (arranged in U or V shape) are switched on the flow of force. As an alternative, it is basically also possible to design the preferably U or V shaped spacer as a hinge without or with only little spring characteristics.

In an advantageous embodiment the coupling device consists of two mutually lockable extensions in the areas of the flexural spring (series) arrangement in which the additional U or V shaped inner spring element (spacer) is serially connected to the outer individual springs (spring arms). Preferably one of the extensions takes the shape of a hook-like lengthening/lug relative to the one individual spring, whereas the other extension/detent edge in the present case is orientated in extension of an opposite leg of the additional U or V shaped spring element so that the hook-like lengthening/lug can positively engage behind the opposite extension/detent edge and can engage with the same, when the U or V shaped spring element (spacer) is compressed.

According to a different or additional aspect of the invention, the clip of the straight branch design preferably is an aneurysm clip the two opposed clamping portions of which at least in portions include a straightly extending beam preferably trimmed with teeth or corrugation.

Another or additional aspect of the invention provides that at the proximal end of each actuating portion a respective stop face/stop plate is formed which are adjacent to each other when the clip is completely opened (bent open), i.e. when the stop plates are compressed and thus prevent further opening of the clip. This constitutes a structurally simple measure against overstretching of the flexural spring and thus a protection against material fatigue or spring fracture. Moreover, the clip can be maintained in the open position in a simple manner by holding the two stop plates together for example by a clamp.

The surgical clip according to the invention in accordance with another or additional aspect is a sheet component which is machined preferably by punching or laser-cutting. Moreover, the surgical clip according to the invention can also be manufactured by injection molding. The flexural spring can further be made of separate spring steel and can be connected to the two clip branches preferably by soldering or welding in one (material) piece. Alternatively, the surgical clip can be integrally made of one single material and can be heat-treated e.g. in portions according to its function.

BRIEF DESCRIPTION OF THE DRAWING FIGURES

Hereinafter the invention will be illustrated by way of a preferred embodiment with reference to the accompanying figures.

Figure 2:
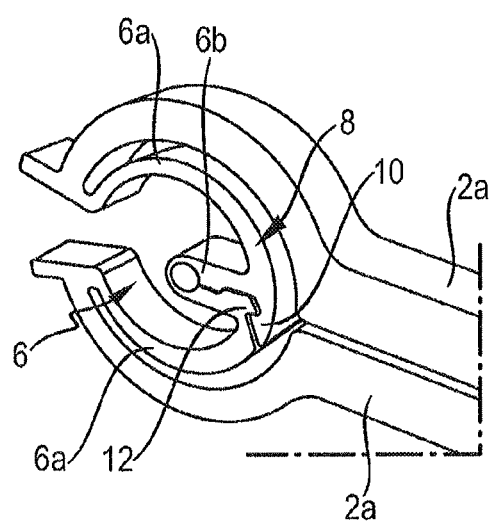
Figure 3:
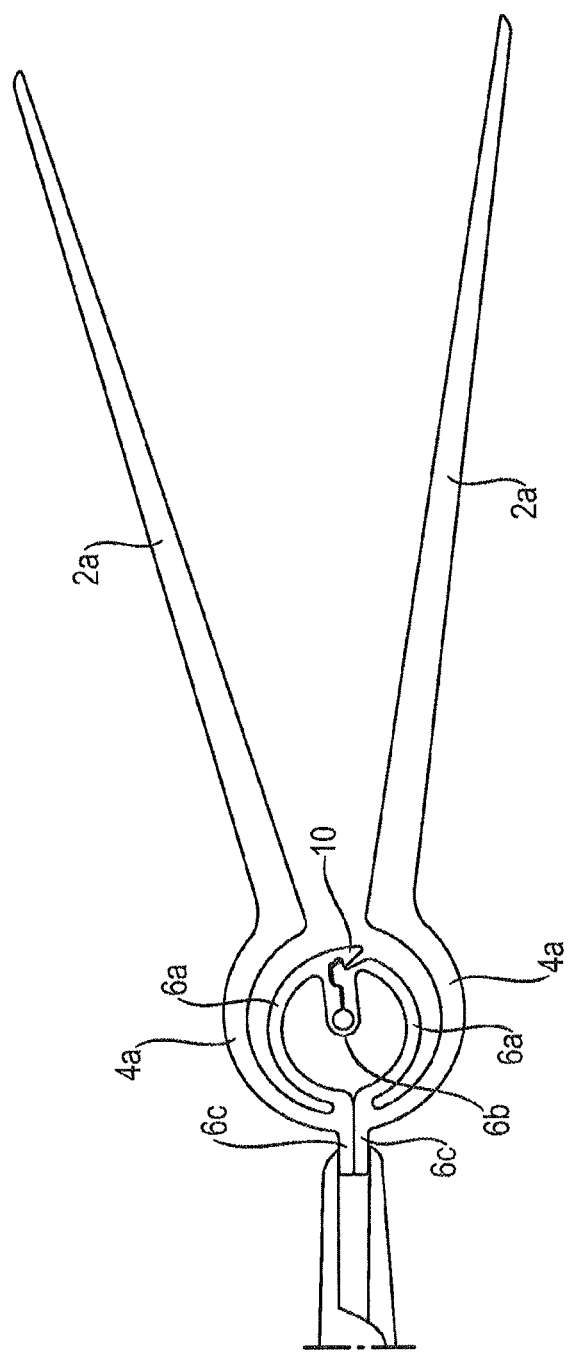

FIG. 1 shows a surgical clip (or tissue clip) according to the invention of the straight branch design for example for use as aneurysm clip in the manufacturing position and thus tensionless (with opened coupling device), FIG. 2 shows an enlarged view of the surgical clip according to FIG. 1 in (tensioned) clamping position (with closed coupling device and thus in closed as-designed position of the clip) and FIG. 3 shows the surgical clip according to FIG. 2 in (tensioned) open position (with closed coupling device).

DETAILED DESCRIPTION

The surgical clip according to a preferred embodiment of the invention includes two clip branches 1 each at least consisting of a clamping portion 2 and an actuating portion 4 as well as a flexural spring or flexural spring (series) arrangement 6 connecting the clip branches 1 which is indented or bulges preferably in C, U or V shape at least over a partial area along (inside/between) the actuating portions 4 toward the clamping portion 2.

The clamping portion 2 of each clip branch 1 according to FIG. 1 comprises a substantially straight elongate clamping bar 2a which is preferably trimmed with a toothing or provided with a corrugation on a side facing the other clamping bar 2a (not shown in detail). However, it can as well be configured to have a rough surface or simply only a smooth (non-machined) surface. The clamping portions 2 can also have a completely different shape, such as a jaw-like shape.

The front (distal) free ends of each clamping bar 2a are rounded or provided with a protective cap especially in the case of the straight design in order to prevent injuries. Moreover, each clamping bar 2a can be provided or configured with a reinforcing strip preferably on a side facing away from the other clamping bar 2a, the reinforcing strip ensuring higher flexural strength of each clamping bar 2a at least in the clamping or operating direction.

At the rear (proximal) end of each clamping bar 2a the actuating portion 4 is axially connected in the form of a presently circular curved actuating bar (yoke) 4a while forming an (obtuse) angle such that the two opposed actuating bars 4a of the clip in the direction of extension thereof almost completely enclose a circular spacing zone.

In the shown embodiment the actuating bars 4a are substantially elongated and non-profiled. However, they can also have an (e.g. slightly corrugated/rolling) longitudinal shape adapted to the human hand (fingers) at least on their respective far (external) sides or an actuating key (not shown) can be attached (soldered/bonded) to the actuating bars 4a.

In accordance with the invention, the actuating bars 4a are configured to be rigid and in one material piece with the clamping bars 2a. That is, the actuating bars 4a are provided to not (only negligibly) deform (distort) elastically/plastically upon actuation of the surgical clip. Thus in the preferred embodiment they constitute no part or component of the flexural spring arrangement 6 but exclusively serve for force transmission of the spring force to the clamping portions 2. As an alternative to this, they can also have at least a particular bending elasticity over the entire length thereof (viz. belong to the flexural spring arrangement) or can be configured to be elastic only over a partial length, preferably the rear bar zone, and thus partially pertaining to the flexural spring arrangement.

The free rear (proximal) ends of the actuating bars 4a are converted into the flexural spring or a part (portion) of the flexural spring (series) arrangement 6 while forming a respective stop plate 6c. The two stop plates 6c are orientated relative to each other so that they are located over the whole surface on top of each other upon actuating the actuating bars 4a and thus they constitute an actuating stop. At the same time the stop plates 6c protrude at an angle from the actuating bars 4a in the proximal direction so that hereby acting portions for an external clamp (cf. FIG. 3) are provided by which the stop plates 6c can be compressed so as to temporarily maintain the clip mechanically in open position.

In this context it is noted that the surgical clip according to the present invention is shown in FIG. 1 in the manufacturing position, i.e. in a position at the time of its fabrication in a non-tensioned state. In this state the two clip branches 1 extend substantially in parallel to each other, wherein the flexural spring (series) arrangement 6 is adjacent at the proximal end of the actuating portions 4 in one material piece as well as non-tensioned in the present case.

Hereinafter the flexural spring (series) arrangement 6 is described in detail by way of FIG. 1.

The flexural spring (series) arrangement 6 presently consists of two outer spring arms or spring portions 6a the respective proximal ends of which are connected to the corresponding actuating portions 4/actuating bars 4a at the proximal ends thereof. The outer spring arms 6a extend along the actuating portions 4 in the distal direction and, while maintaining a substantially uniform clearance, follow the (arc) shape of the actuating bars 4a. However, there is basically the option of the shape of the outer spring arms 6a deviating from the shape of the actuating bars 4a. It is of advantage, however, when as in the present embodiment the free distal end of the outer spring arms 6a move toward each other and thus reduce the distance from each other. Hence in the joint layout they take approximately a U, V or C shape.

The two outer spring arms 6a are coupled at their respective free distal ends/end portions via a spacer, preferably an inner spring portion 6b (in one material piece). The inner spring portion 6b per se has equally a U, V or C shape and bulges in the proximal direction. That is, the two spring legs of the inner spring portion 6b equally extend in the distal direction toward the clamping portions 2 and terminate at the connecting point with the outer spring arms 6a. In this way, substantially a W or ω shape having two outer long spring arms 6a and two serial inner short spring legs 6b is imparted to the flexural spring (series) arrangement 6 according to the preferred embodiment of the invention. As an alternative to this, it is also possible, however, to configure the spacer merely as a hinge without (or only with little) inherent spring characteristics.

Moreover the flexural spring (series) arrangement 6 is equipped with a coupling mechanism (coupling device) 8 for biasing the outer spring arms 6a and possibly for varying the active spring length, as will be described hereinafter by way of FIG. 2.

In the present case, the coupling device 8 consists (is formed) of a detent mechanism integrally formed (in one material piece) with the flexural spring (series) arrangement 6 by means of which the spacer (the inner spring portion 6b or hinge) can be so-to-speak short-circuited while the outer spring arms 6a are elastically deformed.

In other words, the detent mechanism 8 includes a hook-like lug 10 extending from the distal end of one of the outer spring arms 6a in the direction of the distal end of the other outer spring arm 6a and a detent strip 12 formed at the other outer spring arm 6a and constitutes sort of an extension to the connected spring leg of the inner spring portion 6b (spacer). The length (longitudinal extension) of the lug 10 is dimensioned so that for positive engagement behind the detent strip 12 the inner spring portion (i.e. the two inner spring legs) has to be compressed elastically (plastically in the case of a hinge), whereby the two outer spring arms 6a are moving toward each other in a spring-biased manner at the distal free ends thereof. The engaged state of the coupling device 8 occurring in this way is shown in FIG. 2.

In this state not only the inner spring portion 6b is so-to-speak short-circuited (i.e. removed from the flow of force of the flexural spring (series) arrangement 6) so as to possibly vary the spring characteristic of the flexural spring (series) arrangement 6, but the outer spring arms 6a now are also biased, thereby the clamping force being (additionally) increased to the clamping portion in the closed position.

In order to open the medical clip, as is shown in FIG. 3, the two stop plates 6c are moved toward each other against the spring force when the coupling device 8 is closed, thereby the clamping portions 2a being spaced apart. In order to maintain the open position an additional clamp can be attached to the stop plates 6c for holding the latter together.

Theoretically there is also the possibility, however, of first manually disengaging the coupling device 8 by pressing the lug 10 out of the engagement with the detent strip 12, whereby the inner spring portion 6b is connected into the flow of force of the flexural spring (series) arrangement 6 again. In this way the two distal free ends of the outer spring arms 6a are spaced apart from each other and the bias is released. Now in this state the clip can be slightly opened against the no more biased flexural spring (series) arrangement 6 which is more flexible by reversing the short-circuit and can be maintained in the maximum position by means of the clamp (see FIG. 3) which is attached to the now adjacent stop plates 6c.

It is finally mentioned that the clip according to the invention is preferably manufactured as injection-molded part (including the spring arrangement). It can also be manufactured, however, as a sheet member of one single material for example by punching, wire-eroding or laser-cutting especially in the form shown in FIG. 1 and preferably can be hardened at least in the areas provided as flexural springs so as to achieve particular spring elasticity. Alternatively it is also possible to manufacture the spring arrangement at least consisting of the outer spring arms 6a and the spacer (inner spring portion 6b) or together with the actuating bars 4a separately from the clamping portions 2 of spring steel (e.g. by cutting, punching or laser-cutting) and then to connect it to the clamping portions 2, for example by welding or hard-soldering.

The layout shape of the two outer spring arms 6a illustrated in FIGS. 1 to 3, viz. C or circular-arc shaped, moreover has the advantage that a substantially continuously constant flexural stress is realized in the spring arms 6a, whereby the material properties can be exploited at the best. In addition, the closing force is kept very constant due to reproducible manufacturing processes.

Summing up, there is disclosed a surgical clip comprising two clip branches 1 each consisting of a preferably straightly extending (bar-shaped) clamping portion 2 and an actuating portion 4 as well as comprising a flexural spring arrangement 6 via which the two clip branches are coupled to each other preferably in one piece. In accordance with the invention, the flexural spring arrangement 6 is arranged and formed at least in sections (centrally) so that it bulges between the clip branches 1 along the actuating portions 4 in the direction of the clamping portions 2. Irrespective thereof, the flexural spring arrangement 6 is structured by a number of serially coupled individual spring arms extending in opposite directions. Moreover, the flexural spring arrangement includes a coupling mechanism for selectively short-circuiting at least one portion of the spring arrangement to obtain a spring bias in the as-designed position and for varying the spring characteristics, where necessary.

The clamping portion is preferably defined as the axial portion of a branch which upon movement of the pertinent (adjacent) actuating portion toward the opposite actuating portion moves away from the opposite clamping portion. The pivot point of the two branches is defined by the spring arms of the flexural spring arrangement connecting the two clip branches and preferably additionally by the actuating portions which are spring-elastic at least over a partial or complete length.

The invention claimed is:

1. A surgical clip comprising:
   two clip branches, each clip branch comprising:
      a clamping portion;
      an actuating portion; and
      a flexural spring arrangement by which the clip branches are coupled,
   the flexural spring arrangement including a coupling device by which the portions of the flexural spring arrangement can be short-circuited for biasing the surgical clip initially non-tensioned in the manufacturing position, and
   the surgical clip is made integrally of one material piece,
   wherein the flexural spring arrangement bulges at least in sections between the clip branches along the actuating portions toward the clamping portions and forms at least two outer spring arms extending along the actuating portions,
   wherein the at least two outer spring arms are connected to the actuating portions in one material piece at their proximal ends and are coupled to each other at their free distal ends orientated toward the clamping portions so that the at least two outer spring arms jointly form substantially a U, C or V shaped layout, and wherein the flexural spring arrangement includes a U, C or V shaped spacer, an inner spring portion by which the free distal ends of the at least two outer spring arms are interconnected in an unbiased manner and which bulges in the proximal direction.

2. The surgical clip according to claim 1, wherein the coupling device is arranged between the at least two outer spring arms so as to short-circuit the latter in the engaged state at least in portions.

3. The surgical clip according to claim 1, wherein the coupling device is positioned and/or dimensioned along the flexural spring arrangement so that for engaging the latter elastic bending of at least one of the at least two outer spring arms directly to be coupled to each other is required for generating or increasing a spring bias.

4. The surgical clip according to claim 1, wherein the clip branches can be biased by short-circuiting the coupling device in a closing direction of the clip.

5. The surgical clip according to claim 1, wherein upon engagement, the coupling device interconnects the at least two outer spring arms at the distal ends thereof in a spring-elastic and direct manner.

6. The surgical clip according to claim 1, wherein the coupling device is arranged or configured in an area of the free distal ends of the at least two outer spring arms so that the spacer can be short-circuited by the coupling device.

7. The surgical clip according to claim 1, wherein the coupling device includes a manually operable detent mechanism for engaging and disengaging the coupling device.

8. The surgical clip according to claim 7, wherein the detent mechanism includes a hook-like lug extending in one material piece from the free distal end of one of the at least two outer spring arms toward the free distal end of the other of the at least two outer spring arms on which an undercut is configured in the form of a one-material detent edge which can be engaged in the lug.

9. The surgical clip according to claim 1, wherein the coupling device is dimensioned so that for engagement thereof the inner spring portion to be accordingly short-circuited needs to be compressed, wherein simultaneously the at least two outer spring arms retained in a flow of force are biased in a closing direction of the clip.

10. The surgical clip according to claim 1, wherein the surgical clip is of a straight branch design, with each of the clamping portions having a straightly extending clamping bar including a toothed or corrugated trimming.

11. The surgical clip according to claim 1, wherein each of the two actuating portions constitutes an actuating bar which is rigid over its entire length or partial length relative to the flexural spring arrangement, wherein on each actuating bar proximally a stop plate is provided which abut against each other upon reaching a maximum actuating path for delimiting a flexural load.

12. The surgical clip according to claim 1, wherein the surgical clip is a sheet member manufactured by punching or laser-cutting.

13. The surgical clip according to claim 1, wherein the flexural spring arrangement is fabricated of a spring steel separately from the clip branches and is connected in one material piece to the clip branches by soldering or welding or that the clip including the flexural spring arrangement is integrally made of one single material.

14. A surgical clip comprising:
two clip branches, each clip branch comprising:
a clamping portion;
an actuating portion; and
a flexural spring arrangement by which the clip branches are coupled,
the flexural spring arrangement including a coupling device by which portions of the flexural spring arrangement can be short-circuited for biasing the surgical clip initially non-tensioned in a manufacturing position,
the surgical clip being in one material piece,
wherein the flexural spring arrangement bulges at least in sections between the clip branches along the actuating portions toward the clamping portions and forms at least two outer spring arms extending along the actuating portions,
wherein the at least two outer spring arms are connected to the actuating portions in one material piece at their proximal ends and are coupled to each other at their free distal ends orientated toward the clamping portions so that the at least two outer spring arms jointly form a substantially U, C or V shaped layout, and
wherein the flexural spring arrangement includes a U, C or V shaped spacer, an inner spring portion by which the free distal ends of the at least two outer spring arms are interconnected in an unbiased manner and which bulges in a proximal direction.

15. The surgical clip according to claim 14, wherein the coupling device is dimensioned so that for engagement thereof the inner spring portion to be accordingly short-circuited needs to be compressed, whereby simultaneously the at least two outer spring arms retained in a flow of force are biased in a closing direction of the surgical clip.

16. A surgical clip comprising:
two clip branches, each clip branch comprising:
a clamping portion;
an actuating portion; and
a flexural spring arrangement by which the clip branches are coupled,
the flexural spring arrangement including a coupling device by which portions of the flexural spring arrangement can be short-circuited for biasing the surgical clip initially non-tensioned in a manufacturing position, the flexural spring arrangement forming at least two outer spring arms,
the surgical clip being in one material piece,
wherein the coupling device includes a manually operable detent mechanism for engaging and disengaging the coupling device, and
wherein the detent mechanism includes a hook-like lug extending in one material piece from a free distal end of one of the outer spring arms toward a free distal end of the other of the outer spring arms on which an undercut is configured in the form of a one-material detent edge which can be engaged in the lug.

* * * * *